United States Patent [19]

Meibauer

[11] 4,338,957

[45] Jul. 13, 1982

[54] DENTAL PROPHYLAXIS DEVICE AND PROCESS

[76] Inventor: Robert H. Meibauer, 1106 Channel Club Dr., Monmouth Beach, N.J. 07750

[21] Appl. No.: 204,222

[22] Filed: Nov. 5, 1980

[51] Int. Cl.³ ............................................ A61C 15/00
[52] U.S. Cl. ........................................ 132/91; 132/93
[58] Field of Search ..................... 132/91, 92 R, 92 A, 132/90, 93, 89; 46/61; 273/58 C

[56] References Cited

U.S. PATENT DOCUMENTS

| | | | |
|---|---|---|---|
| 795,960 | 8/1905 | Cook | 273/58 C |
| 2,598,275 | 5/1952 | Lakin | 15/167 R |
| 2,601,567 | 6/1952 | Steinberg | 15/167 R |
| 3,421,524 | 1/1969 | Waters | 132/92 R |
| 3,534,745 | 10/1970 | Waters | 132/92 R |
| 3,552,022 | 1/1971 | Axelsson | 433/122 |
| 3,667,454 | 6/1972 | Prince | 15/167 R |
| 3,667,483 | 6/1972 | McCabe | 132/92 A |
| 3,759,274 | 9/1973 | Warner | 132/92 R |
| 3,828,804 | 8/1974 | Ely | 132/91 |
| 3,835,872 | 9/1974 | Daniel | 132/92 R |
| 3,901,251 | 8/1975 | Johnston | 132/91 |
| 3,927,686 | 12/1975 | Zambito | 132/91 |
| 4,014,354 | 3/1977 | Garrett | 132/90 |
| 4,121,829 | 10/1978 | Petrusek | 273/58 C |
| 4,162,687 | 7/1979 | Lorch | 132/91 |

Primary Examiner—Gene Mancene
Assistant Examiner—John J. Wilson

Attorney, Agent, or Firm—Morgan, Finnegan, Pine, Foley and Lee

[57] ABSTRACT

There is disclosed a dental prophylaxis device which may be electrically or battery powered and which comprises in combination a pair of spaced tynes disposed on a housing provided with an axial cavity, stationary support means on the housing in the vicinity of the base of the tynes and oscillating support means located on the housing between the bases of the tynes. The oscillating support means is supported on a cylindrical sleeve disposed in the housing cavity and cooperates with an oscillating drive shaft powered by driving means located in a second housing to which the first mentioned housing is removably connectable. A dental tape or floss having a non-elastic loop at one end which is supported on the oscillating support means and an elastic loop at the opposite end which is supported on the stationary support means spans the space between the ends of tynes and reciprocates between the tynes when the oscillating support means is in motion.

The process disclosed comprises contacting dentition surfaces with a dental tape or floss having a thread segment with a non-elastic loop at one end and an elastic loop at the opposite end, reciprocating the thread segment over the dentition surfaces while expanding and contracting the elastic loop in response to the application of tensile force to the floss and absorbing the tensile force imparted thereto when it encounters resistance and the elastic loop expands.

21 Claims, 7 Drawing Figures

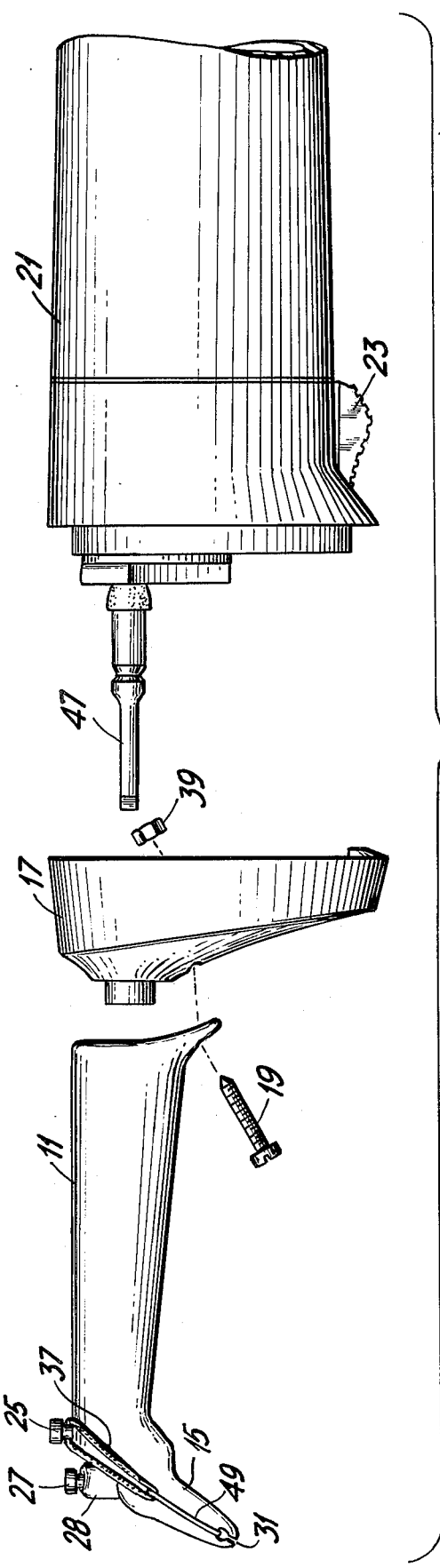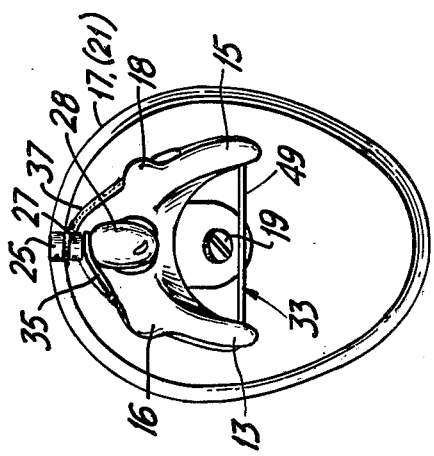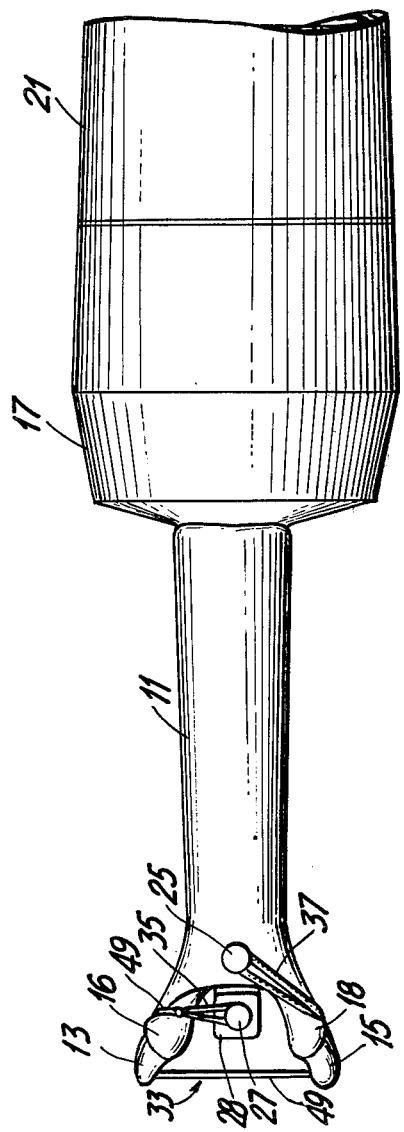
FIG. 2
FIG. 4
FIG. 3

DENTAL PROPHYLAXIS DEVICE AND PROCESS

This invention relates to a dental prophylaxis process and a device for accomplishing the same. More particularly, the invention relates to a dental flossing process and a mechanical device for the flossing of dentition surfaces.

BACKGROUND OF THE INVENTION

It is well known in the field of dentistry that failure to remove plaque from dentition surfaces and debris from between dentitions is a principal cause of dental diseases, such as tooth decay and gingivitis and the like. Removal of plaque and debris by brushing is the commonest and easiest method known. However, brushing is generally inadequate, especially when self-administered. A more efficient and known technique is the cleaning of the dentition surfaces and areas between such surfaces by using a dental tape or floss which is moved reciprocally over and between the dentition surfaces. Furthermore, the reciprocating motion of the floss as it is manipulated over and between the dentition surfaces is beneficial as a treatment for and prevention of periodontal diseases, such as gingivitis and the like. This is so since the free margin of the gingiva which is adjacent to the individual teeth of the dentition and forms the gingival sulcas can be readily reached by dental floss, although it is generally inaccessible to a brush or other instruments, and the sulci are subject to the invasion of plaque or colonies of bacteria which cause diseases of these tissues. Thus, floss, in general, is particularly beneficial in removing plaque and debris, as well as serving, in addition, as a vehicle for the application of medication. On the other hand, dental tape or floss is inconvenient and awkward to handle.

Consequently, much development has been undertaken in the past to provide dental tape or floss in various forms which is more convenient to handle and use. In addition, much development has taken place to provide mechanical devices for the flossing of dentition surfaces. Therefore, past developments have broadly involved the provision of dental tape or floss in various forms to render the same more easy to use and the provision of mechanical devices to support or hold the dental tape or floss in a manner so that it can be employed with greater efficiency and facility.

As an example of such developments, U.S. Pat. No. 4,162,687 discloses a flossing device which is manipulated by hand and provided with a pair of spaced, resilient arms having fingers extending therefrom. The fingers are equipped with knobs on their distal ends and a length of dental tape or floss having a grommet on each end is disposed over the knobs on the ends of the fingers. A somewhat similar device, but which is power driven, is disclosed in U.S. Pat. No. 4,014,354 in which the dental tape or floss is tensioned between a pair of L-shaped arms attached to a handle which is adapted to be driven by the power element. On the other hand, U.S. Pat. No. 3,927,686 discloses a hand manipulated flossing device which includes a handle and an adjustable head provided with a single strand or a plurality of strands of dental tape or floss.

Still another dental cleaning device is disclosed in U.S. Pat. No. 3,835,872 in which a flexible dental tape or floss is disposed on a handle having a detachable yoke for tautly supporting a run of the tape, the tape being attached to a pair of anchor pins disposed on the handle and one of which is disposed on a reciprocable trigger mounted in the handle for the purpose of tensioning the tape. The tape per se is provided with non-elastic loops at each end which are disposed over the previously mentioned pins. U.S. Pat. No. 3,828,804 discloses still another apparatus which is a hand manipulated device for cleaning teeth that includes a handle with a nub disposed thereon and which is provided with extending, spaced arms having notches at the ends thereof. An endless or circular elastomeric dental floss or tape is disposed in the notches thereby passing across the space between the arms and around the nub. In a variation of the device a simple length of elastomeric band is anchored in the notches of the arms by means of shims or heads.

A further dental cleaning instrument is disclosed in U.S. Pat. No. 3,759,274 in which a strand of dental floss is mounted on an extended fork which supports the strand and permits an oscillating movement which is imparted thereto by a drive means. In addition, the device also includes a spool for carrying the strand and for registering a new, unused portion of the strand for use in each subsequent cleaning cycle. A still further dental cleaning device is shown in U.S. Pat. No. 3,667,483 in which the device includes a pair of projecting arms disposed on a support frame, the arms being provided with guides at their outer ends to receive and permit relative movement of floss which passes from a spool to a take-up reel mounted on the supporting frame. The floss is driven in a reciprocating manner through a drive means located in the support frame and the device is provided with means to alternately remove floss from the supply spool and feed it to the take-up spool after each use.

In U.S. Pat. No. 3,552,022 there is disclosed another powered dental cleaning or polishing device in which a tool having a conical stem portion is adapted to be inserted in and removed from a handle in which a reciprocating socket is provided therefor. The operating end of the tool is wedgelike and pointed, two broad sides being rough in order to abrade dentition surfaces and a third side thereof being narrow and smooth in order to prevent injury to the gingiva. Another power driven cleaning device is disclosed in U.S. Pat. No. 3,534,745. The device includes a housing provided with spaced prongs and a dental tape or floss holder and supply unit adapted to be removably attached to a power unit which imparts reciprocating motion to the tape as well as permitting the feeding of new tape to the unit after each use. Finally, U.S. Pat. No 3,421,524 discloses a power driven dental cleaner including a power unit which is adapted to receive a cleaning unit which includes an elongated shaft provided with a pair of spaced tynes. A dental tape or floss supply holding member is removably positioned on the power unit and the dental tape or floss is fed therefrom through an eyelet in each of the tynes and back to the supply holding member where it is taken up on a take-up spool.

While the various devices disclosed in the above-mentioned patents are useful for cleaning dentition surfaces, they still exhibit various disadvantages. For example, many of them are extremely complex in structure and consequently relatively expensive to manufacture. In addition, many of the known structures are relatively difficult to employ, often being difficult to load and require complex adjustment to impart the required tenseness to the dental tape or floss utilized therewith.

In addition, many of the known devices, such as those referred to above, are not provided with means to automatically stop the movement of the floss should it become caught or jammed on the dentition surfaces. Furthermore, due to their particular construction, many of the known devices do not provide maximum contact of the floss with the dentition surfaces to be cleaned and, in addition, due to their construction, necessitate the use of more than the needed amount of dental tape or floss for carrying out a given cleaning operation. There exists, therefore, the need for a dental prophylaxis device and a process for dental prophylaxis which do not exhibit the above-mentioned disadvantages. The present invention fulfills this need.

BRIEF STATEMENT OF THE INVENTION

In accordance with the invention there is provided a device for dental prophylaxis which in its broadest terms comprises in combination housing means provided with an axial cavity and having a pair of spaced tynes provided with slotted openings disposed thereon and projecting outwardly therefrom, stationary support means on the housing in the vicinity of the base of each of the tynes, and oscillating support means located on the housing between the bases of the tynes and which is supported on a cylindrical sleeve that is disposed axially within the cavity of the housing, the housing means being adapted to be connected to driving means to drive the oscillating support means through the cylindrical sleeve.

In a more detailed aspect, a device for dental prophylaxis in accordance with the invention includes second housing means removably connected to the above-mentioned or first housing means, the second housing means being provided with internal driving means including an external, axially projecting, oscillating drive shaft which projects axially into the first housing means and engages the cylindrical sleeve disposed in the cavity thereof.

In still further detailed aspect, a dental prophylaxis device in accordance with the invention further includes dental tape or floss comprising a thread segment having a non-elastic loop at one end and an elastic loop at the opposite end, the dental floss being supported in the slotted openings of the above-mentioned tynes and across the space therebetween with the elastic loop being supported on the stationary support means and the non-elastic loop being supported on the oscillating support means.

Further, in accordance with the invention, the dental prophylaxis process comprises contacting dentition surfaces to be treated with a dental floss having a thread segment which is provided with a non-elastic loop at one end and an elastic loop at the opposite end, reciprocating the thread segment over the surfaces of the dentition to be treated, while expanding and contracting the elastic loop in response to the application of tensile force to the dental floss as it reciprocates over the dentition surfaces and absorbing the tensile force which is imparted to the dental floss when it encounters resistance as it reciprocates over the dentition surfaces and the elastic loop expands.

Expressed in more detailed terms, the dental prophylaxis process, according to the invention, comprises contacting dentition surfaces to be treated with a dental floss having a thread segment that is provided with a non-elastic loop at one end and an elastic loop at the opposite end, reciprocating the thread segment over the dentition surfaces and across the space between a pair of spaced, stationary tynes which bracket the dentition surfaces while imparting oscillating movement to the dental floss through the non-elastic loop along an axial line which is substantially at a right angle to the axis of reciprocation of the thread segment and while expanding and contracting the elastic loop in response to the application of a tensile force to the dental floss as it reciprocates over the dentition surfaces, and absorbing the tensile force imparted to the dental floss when it encounters resistance as it reciprocates over the dentition surfaces and the elastic loop expands.

THE DRAWINGS

In order to describe the device and process of this invention more fully, reference is directed to the accompanying drawings which are to be taken in conjunction with the following description and in which drawings:

FIG. 2 is a partial, elevational, exploded view of the prophylaxis device illustrated in FIG. 1;

FIG. 3 is a partial plan view of the prophylaxis device shown in FIG. 1;

FIG. 4 is a front end view in elevation of the device of FIG. 1;

Figure 1:
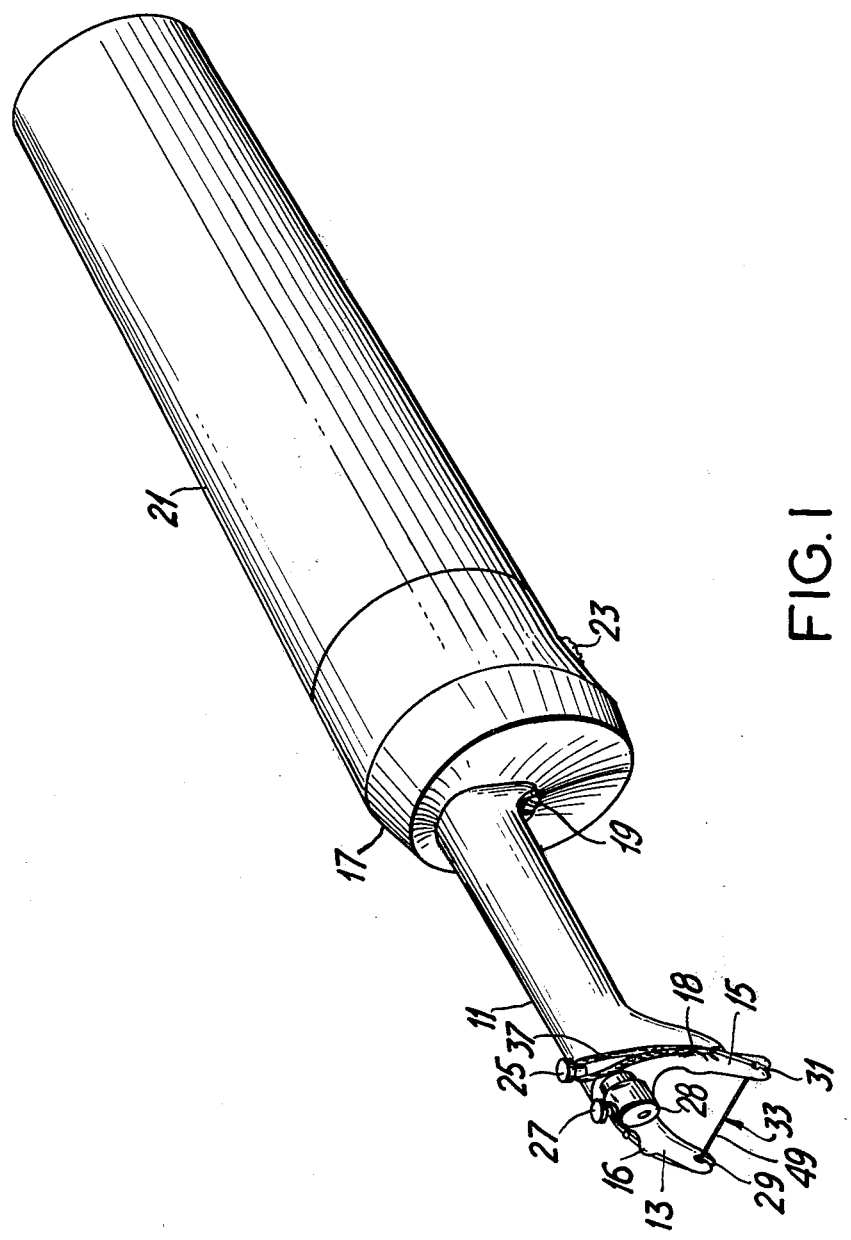
FIG. 1 is a view in perspective of a dental prophylaxis device according to the invention.
Figure 6:
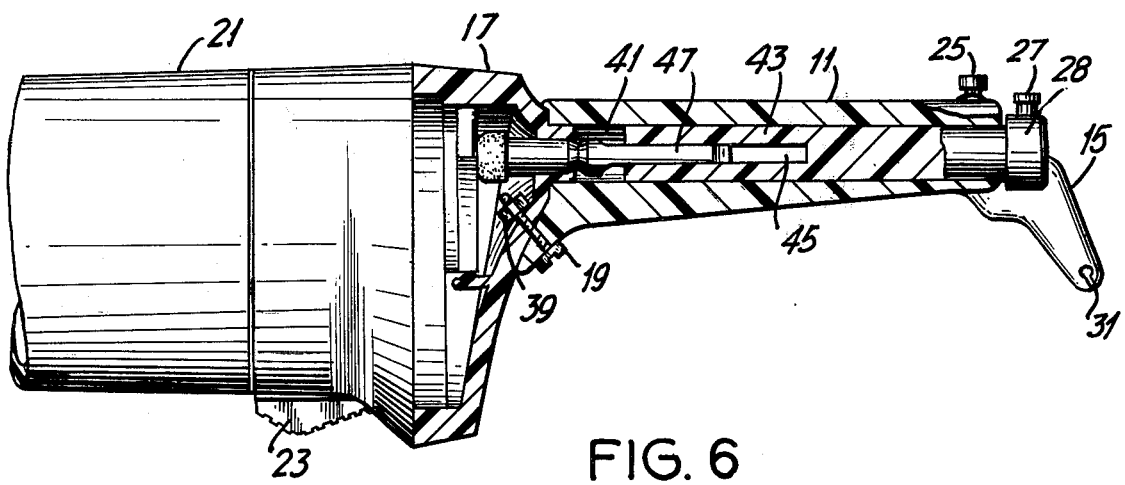
Figure 7:
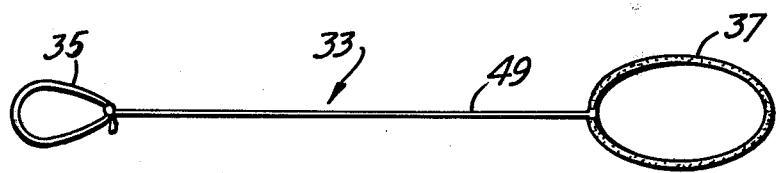

FIG. 6 is a partial elevational view of the device shown in FIG. 1, partially in section, illustrating in detail the cylindrical sleeve disposed within the housing cavity and the oscillating drive shaft engaging the sleeve; and FIG. 7 is a plan view of dental flossing thread in accordance with the invention having a thread segment with a non-elastic loop at one end and an elastic loop at the opposite end.

DESCRIPTION OF THE PREFERRED EMBODIMENTS

Figure 5:
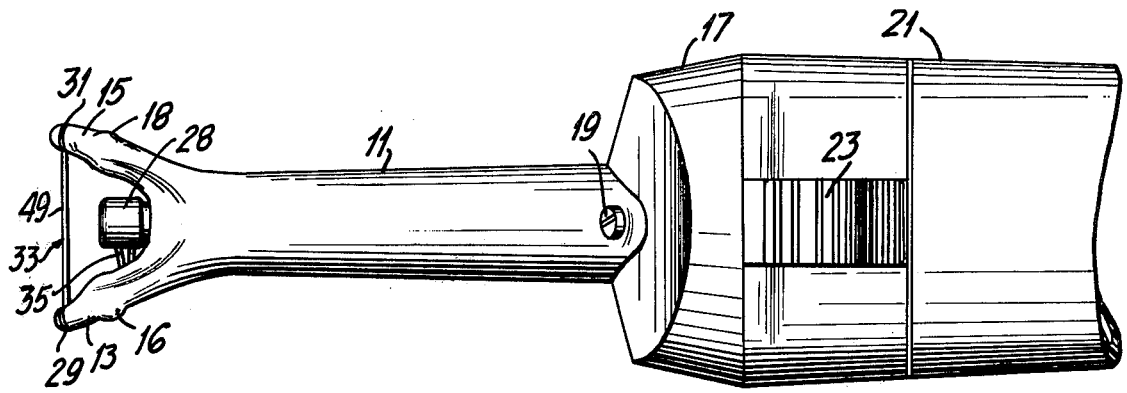
FIG. 5 is a partial bottom view of the device illustrated in FIG. 1.

Referring now to FIG. 1, a dental prophylaxis device according to the invention comprises an elongated, generally tubular housing 11 having a pair of tynes 13 and 15 disposed thereon at one end and provided with guide grooves 16 and 18, respectively, on the shoulder thereof. At the opposite end, the housing is adapted to be connected to a collar 17 by any convenient means, such as a screw 19 or the like. In turn, collar 17 is adapted to be snap-fitted or friction-fitted to second housing means 21 containing suitable driving means to impart oscillating motion to a drive shaft or the like as explained more fully hereinbelow and, optionally, a power source such as a rechargeable battery (not shown). Alternatively, the second housing may be adapted in a convenient manner to be connected to an electrical outlet by means of a suitable electrical cord and plug (not shown) in order to energize the device. The second housing means is also provided with a switch 23, more particulary seen in FIG. 5, for activating or deactivating the device.

Housing means 11 has a stationary support means 25, such as a post, located on its upper surface substantially midway between the bases of the tynes 13 and 15, as more particularly shown in FIG. 3. In addition, oscillating support means 27, such as a post, is located on the front end of housing 11 between the bases of the tynes, as more particularly shown in FIG. 4. The oscillating support means is attached in a convenient manner, such as with a hub 28, to one end of a cylindrical sleeve disposed axially within the housing, as explained more fully hereinafter.

As shown in FIG. 1, tynes 13 and 15 have slotted openings 29 and 31, respectively, into which a dental tape or floss, generally referred to by numeral 33 and provided with loops 35 and 37 at each end, is inserted and anchored on the stationary and oscillating support means. Thus, the dental tape or floss extends across the space between the slotted ends of the tynes as may be seen particularly in FIG. 4.

As illustrated more particularly in FIG. 2, the dental prophylaxis device of this invention comprises, therefore, two fundamental or main elements. These are the housings 11 and 21 which are cooperatively joined to each other by collar 17. In this connection, it is to be understood, however, that housing 11 may be shaped so that the collar 17 is an integral portion thereof and adapted to be friction-fitted directly to housing 21, thus eliminating the need for separate collar 17, screw 19 and its mating nut 39.

As may be seen in FIG. 6, housing 11 has a generally elongated internal cavity 41 in which a generally elongated hollow cylindrical sleeve 43 having oscillating support means 27 fixed thereon is axially disposed, the sleeve being of slightly smaller overall diameter than the internal diameter of the cavity. Thus, the sleeve freely oscillates in the cavity and imparts oscillating motion to support means 27. As illustrated, sleeve 43 is also provided with an internal cavity 45 which may extend either partly through the length thereof, as shown, or completely therethrough. An oscillatable drive shaft 47 projecting from housing 21 and having dimensions sufficiently large to be frictionally engaged within cavity 45 of the sleeve is disposed in that cavity to impart oscillating motion to the sleeve when the driving means is in motion.

Turning next to FIG. 7, dental tape or floss, generally designated by numeral 33, in accordance with this invention comprises a thread segment 49, a loop 35 which is non-elastic at one end and a second loop 37 which is elastic at the opposite end. In its disposition on the dental prophylaxis drive of the invention, the thread segment 49 of tape or floss 33 is inserted in the slotted grooves of the tynes and passes through the guide grooves on the shoulders thereof with the non-elastic loop 35 being disposed on the oscillating support means 27 and the elastic loop 37 being disposed on the stationary support means 25 of housing 11.

The various elements of the dental prophylaxis device of this invention, excluding the tape or floss, may be made from a wide variety of materials, either metals or plastics. In general, plastics such as nylon, polyesters and the like are preferred since they can be more readily shaped or molded at a lower cost while still having the required strength.

Insofar as the tape or floss is concerned, it can be made from natural or synthetic thread material, such as, for example, cotton and nylon, and the like with a non-elastic loop attached in any convenient manner to one end and an elastic loop, such as, for example, a rubber band, attached in any convenient manner at the opposite end. Alternatively, and preferably, the tape or floss can be made from a synthetic thread having alternate non-elastic and elastomeric segments cut into the desired premeasured lengths to provide individual lengths of floss having a non-elastic segment and an elastomeric segment at opposite ends and then forming the non-elastic loop and elastomeric loops at each end by employing the respective non-elastic and elastomeric ends turned back upon themselves and joined in any convenient manner.

Due to the unique construction of the device of this invention, it can be marketed for use by the ultimate consuming public as a whole or in parts. For example, an initial purchaser will normally obtain the whole device, that is the housing 11, second housing 21 and at least one dental tape or floss. On the other hand, an ample supply of tapes can also be provided with the initial purchase or sold separately at a later time. Moreover, a consumer who has already undertaken the initial purchase can, as needed, simply purhase at a subsequent time either the housing 11 or housing 21 should replacement parts be needed or desired for one reason or another. For example, where a device is to be employed by a number of individuals in a household, only one housing 21 may be purchased along with an adequate supply of tapes and a sufficient number of housings 11 to accommodate each individual member of the household.

In use, the dental prophylaxis device of this invention operates in the following manner. When the switch 23 on housing 21 is in the "on" position, the device is energized, either through a battery or through electrical means as mentioned above, imparting power to the driving means and oscillating the drive shaft 47. In turn, drive shaft 47 imparts oscillating motion to the cylindrical sleeve 43 and thus oscillates post 27 fixed to hub 28. As a result of such oscillating motion, the thread segment 49 of dental tape or floss 33 disposed across the space between the ends of tynes 13 and 15, and with its non-elastic loop supported on oscillating post 27 and elastic loop supported on stationary post 25, reciprocates between the tynes. Consequently, when the reciprocating thread segment 49 is placed in contact with dentition surfaces to be treated and reciprocates over those surfaces, tensile force is applied thereto by such contact and the elastic loop of the tape expands and contracts in response to such force. Moreover, because of the expansion and contraction of the elastic loop, the thread segment of the tape is provided with the proper tension at all times, thus insuring that the thread segment adjusts to the contour of the dentition surfaces at all times, thereby providing maximum contact of the dental tape with the dentition surfaces. On the other hand, should the tape or floss catch or jam, the elastic loop will further expand, becoming slack, and the reciprocating movement of the tape or floss will cease, even though the power is on and imparting oscillating motion to post 27 on which the non-elastic loop is supported.

Therefore, expressed in other terms, a dental prophylaxis process in accordance with this invention comprises contacting dentition surfaces to be treated with a dental tape or floss having a thread segment provided with a non-elastic loop at one end and an elastic loop at the opposite end, reciprocating the thread segment over the surfaces of the dentition while expanding and contracting the elastic loop in response to the application of tensile force to the tape or floss as it reciprocates over the dentition surfaces and absorbing the tensile force imparted to the dental tape or floss when it encounters resistance as it reciprocates over the dentition surfaces and the elastic loop expands. It is to be noted in this respect that as achieved in the inventive process, reciprocation of the dental tape or floss takes place across the space between the spaced, stationary tynes of the device of the invention which bracket the dentition surfaces being treated. Moreover, in this respect, it is to be further understood that the oscillating movement imparted to the tape or floss, in accordance with the invention, occurs along an axial line substantially at a right angle to the axis of reciprocation of the thread segment of the tape or floss.

In utilizing the device and carrying out the process of this invention, medication may, if desired, be applied to the dental floss and transferred to the dentition surfaces over which the floss reciprocates. Consequently, in this respect, the process of this invention in its more specific aspects also includes the application of such medication to the dentition surfaces being treated.

The dental prophylaxis device and process of this invention present numerous advantages. Among such advantages are those resulting from the unique construction of the dental tape or floss per se. For example, the provision of tape or floss segments having loops at both ends allows easy positive attachment of the floss to the stationary and oscillating posts of the housing without any additional complex means of fixation such as are needed in many of the known flossing devices. Moreover, the tape or floss segments can be manufactured to one pre-measured length sufficient to span the space between the tynes and be arranged over the posts. Thus, a minimum amount of floss is utilized. In addition, replacement tapes or floss can be manufactured and marketed less expensively than tapes suitable for use in known flossing devices.

The utilization of an elastic loop on one end of the tape or floss segment provides "built-in" tension control of the floss, as well as positive return to start position. The positive "built-in" tension control of the tape or floss assures maximum contact of the floss with the dentition surfaces being treated at all times, thus substantially eliminating point to point contact of dentition surface and floss which occurs if the tape is too tense, as is the case in many of the known devices or no action if the tape is too slack. At the same time, however, the proper positive tension provided by the use of the elastic loop on the tape permits the floss to stop reciprocating even though the power is on should the floss become caught or jammed on the dentition surface being treated. Still further, the provision of proper positive tension on the floss by the use of the elastic loop substantially eliminates irritation which often occurs with known flossing devices due to excessive tension imparted to the floss by such devices. Finally, the use of tape or floss segments with looped ends and its ease of attachment or fixing to the device eliminates extensive handling of the tapes and is thus more hygienic.

Insofar as the housings and related elements of the device are concerned, they are relatively easy and inexpensive to manufacture with readily available materials and a plurality of the housing portions provided with the tynes can be sold for use with one driving means. Moreover, the housing portion having the tynes can also be sold separately and adapted for attachment for use with equipment normally found in a dental office. Furthermore, since the tynes are stationary and only the tape or floss reciprocates, the device is easier to employ without the danger of damaging dentition surfaces by contact thereof with the tynes, as is the case with devices which have to be manipulated by hand in the mouth of a user in order to reciprocate or otherwise move the tape or floss.

It is to be understood that the device and process of this invention provide a mechanical flossing means for the removal of plaque on the inter-proximal surfaces of the teeth and, as such, are much more efficient than hand flossing methods. Moreover, the device and process of this invention eliminate many of the problems inherent in previous devices since the tapes or floss can be attached to the mechanical portions of the device in a matter of seconds and the unique structure of the floss loop eliminates previous means of securing floss by winding and the like. Moreover, as mentioned hereinabove, the unique floss segments of this invention can be manufactured in exact lengths, which is usually 2 inches, in order to fit the device. With the device and in accordance with the process the floss moves rapidly and conforms to the contours of the dentition surfaces without loss of speed or creating slack as often occurs in known devices and the entire dentition surface can be flossed efficiently in a matter of minutes. Furthermore the device and process of this invention are harmless to tissue and the tape or floss will stop moving if it becomes jammed on a dental filling or the like. Furthermore, as previously mentioned, the tynes do not move as in some known devices, thus obviating the danger of damaging tissue and dental surfaces by abnormally sharp contact of the tynes therewith.

It is also to be noted that the device can be used advantageously by all age groups, from pre-school age children to adults and moreover, the device can be utilized with great facility by a parent to floss a child's teeth. In addition, the entire device is easily cleaned or sterilized, thus providing hygienic benefits. The loops, due to their low cost, are disposable after use, thus also providing increased hygienic standards.

The reciprocal action of the tape or floss is beneficial in treating and preventing periodontal disease, that is gingivitis since the sulci between the teeth can be reached easily by the dental tape used with the device. Moreover, the mechanical action of the device, in accordance with the process, debrides the tissues of bacterial colonies, necrotic tissue and organic debris, accomplishing this without irritation while at the same time providing a stimulating effect which promotes the formation of the hornified layer of cells that normally protects the underlying tissues from trauma and bacterial invasion. Numerous other advantages of the inventive device and process will be readily apparent to those skilled in the art.

It is it be understood that the descriptive embodiments of this invention set forth herein are illustrative only and the concepts of this invention are not to be limited thereby, except as defined in the appended claims.

What is claimed is:

1. In a device for dental prophylaxis, the combination comprising:

housing means provided with an axial cavity and having a pair of spaced, stationary tynes provided with slotted openings disposed thereon and projecting outwardly therefrom, stationary support means on said housing in the vicinity of the base of said tynes, and oscillating support means located on said housing between the bases of said tynes and supported on a cylindrical sleeve disposed axially within said cavity, said housing means being adapted to be connected to driving means to drive said oscillating support means through said cylindrical sleeve.

2. A device as defined in claim 1 including a collar fixed to the housing means and adapted to be removably connected to second housing means having driving means located therein.

3. A device as defined in claim 2 wherein the driving means includes an external, axially projecting oscillating drive shaft projecting axially into the first mentioned housing means, and engaging the cylindrical sleeve.

4. A device as defined in claim 2 wherein the driving means is electrically powered.

5. A device as defined in claim 2 wherein the driving means is battery powered.

6. In a device for dental prophylaxis, the combination comprising:
first and second housing means removably connected to each other; said first housing means having a pair of spaced, stationary tynes provided with slotted openings, stationary support means on said first housing means in the vicinity of the base of each of said tynes and oscillating support means located on said first housing means between the bases of said tynes and supported on a cylindrical sleeve disposed axially within said first housing means; said second housing means provided with internal driving means, including an external, axially projecting, oscillating drive shaft projecting axially into said first housing means and engaging said cylindrical sleeve.

7. A device as defined in claim 6 wherein the driving means is electrically powered.

8. A device as defined in claim 6 wherein the driving means is battery powered.

9. In a device for dental prophylaxis, the combination comprising:
first and second housing means removably connected to each other; said first housing means having a pair of spaced tynes provided with slotted openings, stationary support means on said first housing means in the vicinity of the base of each of said tynes and oscillating support means located on said first housing means between the bases of said tynes and supported on a cylindrical sleeve disposed axially within said first housing means; said second housing means provided with internal driving means, including an external, axially projecting, oscillating drive shaft projecting axially into said first housing means and engaging said cylindrical sleeve; and dental flossing thread provided with a non-elastic loop at one end and an elastic loop at the opposite end supported in said slotted openings of said tynes and across the space therebetween with said elastic loop being supported on said stationary support means and said non-elastic loop being supported on said oscillating support means.

10. A device as defined in claim 9 wherein each of the pair of spaced tynes is provided with a guide groove on the shoulder thereof.

11. A device as defined in claim 9 wherein the driving means is electrically powered.

12. A device as defined in claim 9 wherein the driving means is battery powered.

13. In a device for dental prophylaxis, the combination comprising:
first and second housing means removably connected to each other; said first housing means having a pair of spaced, stationary tynes provided with slotted openings and a guide groove on the external shoulder of each of said pair of tynes, stationary support means on said first housing means in the vicinity of the base of each of said tynes and oscillating support means located on said first housing means between the bases of said tynes and supported on a cylindrical sleeve disposed axially within said first housing means; said second housing means provided with internal driving means, including an external, axially projecting, oscillating drive shaft projecting axially into said first housing means and engaging said cylindrical sleeve; and dental flossing thread provided with a non-elastic loop at one end and an elastic loop at the opposite end supported in said slotted openings and by said guides of said tynes and across the space therebetween and in an axial line at substantially a right angle to the axis of said cylindrical sleeve, said elastic loop being supported on said stationary support means and said non-elastic loop being supported on said oscillating support means, whereby said dental flossing thread reciprocates between said tynes when said oscillating support means is oscillated by said driving means through the engagement of said drive shaft with said cylindrical sleeve.

14. A device as defined in claim 13 wherein the driving means is electrically powered.

15. A device as defined in claim 13 wherein the driving means is battery powered.

16. A dental floss comprising a thread segment having a non-elastic loop at one end and an elastic loop at the opposite end, said elastic loop being under positive tension at all times and providing tension control of said floss and substantially eliminating point to point contact of dentition and said floss when in use to floss a dentition.

17. A dental prophylaxis process comprising: contacting dentition surfaces to be treated with a dental floss having a thread segment provided with a non-elastic loop at one end and an elastic loop at the opposite end, reciprocating said thread segment over the surfaces of said dentition while expanding and contracting said elastic loop in response to the application of tensile force to said dental floss as it reciprocates over said dentition surfaces and absorbing the tensile force imparted to said dental floss when it encounters resistance as it reciprocates over said dentition surfaces and said elastic loop expands.

18. A process as defined in claim 17 including applying medication to the dental floss and transferring said medication to the dentition surfaces to be treated as said dental floss reciprocates over said dentition surfaces.

19. A process as defined in claim 17 wherein the dental floss reciprocates between a pair of spaced, stationary tynes.

20. A dental prophylaxis process comprising: contacting dentition surfaces to be treated with a dental floss having a thread segment provided with a non-elastic loop at one end and an elastic loop at the opposite end, reciprocating said thread segment over said dentition surfaces and across the space between a pair of spaced, stationary tynes bracketing said dentition surfaces while imparting oscillating movement to said dental floss through said non-elastic loop along an axial line which is substantially at a right angle to the axis of reciprocation of said thread segment and while expanding and contracting said elastic loop in response to the application of tensile force to said dental floss as it reciprocates over said dentition surfaces, and absorbing the tensile force imparted to said dental floss when it encounters resistance as it reciprocates over said dentition surfaces and said elastic loop expands.

21. A process as defined in claim 20 including applying medication to the dental floss and transferring said medication to the dentition surfaces to be treated as said dental floss reciprocates over said dentition surfaces.

* * * * *